United States Patent
Röntgen et al.

(10) Patent No.: US 11,399,776 B2
(45) Date of Patent: Aug. 2, 2022

(54) METHOD FOR IDENTIFYING A FARM ANIMAL HAVING AN IMPAIRMENT OF REGULATIVE CAPACITY IN RESPONSE TO METABOLIC STRESS

(71) Applicant: Leibniz-Institut für Nutztierbiologie, Dummerstorf (DE)

(72) Inventors: Monika Röntgen, Kühlungsborn (DE); Sandra Erdmann, Döbbersen (DE)

(73) Assignee: Leibniz-Institut Fuer Nutztierbiologie, Dummerstorf (DE)

( * ) Notice: Subject to any disclaimer, the term of this patent is extended or adjusted under 35 U.S.C. 154(b) by 26 days.

(21) Appl. No.: 16/649,195

(22) PCT Filed: Sep. 21, 2018

(86) PCT No.: PCT/EP2018/075627
§ 371 (c)(1),
(2) Date: Mar. 20, 2020

(87) PCT Pub. No.: WO2019/057906
PCT Pub. Date: Mar. 28, 2019

(65) Prior Publication Data
US 2020/0214645 A1    Jul. 9, 2020

(30) Foreign Application Priority Data
Sep. 22, 2017 (EP) ..................... 17192564

(51) Int. Cl.
*A61B 5/00* (2006.01)
*G16H 50/30* (2018.01)
(Continued)

(52) U.S. Cl.
CPC ........ *A61B 5/7282* (2013.01); *A61B 5/02405* (2013.01); *A61B 5/4884* (2013.01);
(Continued)

(58) Field of Classification Search
CPC . A61B 5/7282; A61B 5/02405; A61B 5/4884; A61B 5/4035; A61B 2503/40; G16H 50/30; G16H 50/20
See application file for complete search history.

(56) References Cited

U.S. PATENT DOCUMENTS

2004/0019289 A1 * 1/2004 Ross ................ A61B 5/02405
600/519

FOREIGN PATENT DOCUMENTS

| DE | 202012100735 U1 | 6/2013 |
| WO | 2008002941 A2 | 1/2008 |
| WO | 2015168341 A1 | 11/2015 |

OTHER PUBLICATIONS

Asakawa A, Inui A, Kaga T, Yuzuriha H, Nagata T, Fujimiya M, Katsuura G, Makino S, Fujino MA and Kasuga M 2001. A role of ghrelin in neuroendocrine and behavioral responses to stress in mice. Neuroendocrinology 74, 143-147.
(Continued)

*Primary Examiner* — Michael W Kahelin
*Assistant Examiner* — Naveed R. Kolia
(74) *Attorney, Agent, or Firm* — Armstrong Teasdale LLP

(57) ABSTRACT

Described herein is a method for identifying a farm animal having an impairment of regulative capacity in response to metabolic stress, the method including: a) assessing the value of the nonlinear domain heart rate variability component $L_{MAX}$ of a farm animal based on a heart beat interval data set obtained for the farm animal; and b) comparing the value of $L_{MAX}$ assessed according to (a) with a species specific threshold of $L_{MAX}$, whereby a farm animal having an impairment of regulative capacity will be identified.

10 Claims, 3 Drawing Sheets

(51) Int. Cl.
    *G16H 50/20* (2018.01)
    *A61B 5/024* (2006.01)
(52) U.S. Cl.
    CPC .............. *G16H 50/20* (2018.01); *G16H 50/30* (2018.01); *A61B 5/4035* (2013.01); *A61B 2503/40* (2013.01)

(56) References Cited

OTHER PUBLICATIONS

Borell von E, Langbein J, Despres G, Hansen S, Leterrier C, Marchant-Forde J, Marchant-Forde R, Minero M, Mohr E, Prunier A, Valance D and Veissier I 2007. Heart rate variability as a measure of autonomic regulation of cardiac activity for assessing stress and welfare in farm animals - a review. Physiology &. Behavior 92, 293-316.

Börner S, Albrecht E, Schäff C, Hacke S, Kautzsch U, Derno M, Hammon HM, Röntgen M, Sauerwein H and Kuhla B 2013. Reduced AgRP activation in the hypothalamus of cows with high extent of fat mobilization after parturition. General and Comparative Endocrinology, 193,167-177.

Bradford B J, and Allen M S 2008. Negative energy balance increases periprandial ghrelin and growth hormone concentrations in lactating dairy cows. Domestic Animal Endocrinology 34, 196-203.

Brosh, A 2007. Heart rate measurements as an index of energy expenditure and energy balance in ruminants: a review. Journal of Animal Science 85,1213-1227.

Brouwer, E 1965. Report of sub committee on constants and factors. Energy Metabolism. Proc 3rd Symposium 11: 441-443. Troon Uk, EAAP. Blaxter, K. L.

Cabiddu R, Cerutti S, Viardot G, Werner S and Bianchi AM 2012. Modulation of the sympatho-vagal balance during sleep: frequency domain study of heart rate variability and respiration. Frontiers in Physiology 3, 45. doi: 10.3389/fphys.2012.00045.

Chilliard Y, Bocquier F and Doreau M 1998. Digestive and metabolic adaptations of ruminants to undernutrition, and consequences on reproduction. Reproduction Nutrition Development 38, 131-152.

Clabough DL and Swanson CR 1989. Heart rate spectral analysis of fasting-induced bradycardia of cattle. American Journal of Physiology 257, R1303-R1306.

Davidson JA and Beede DK 2009. Exercise training of late-pregnant and nonpregnant dairy cows affects physical fitness and acid-base homeostasis. Journal of Dairy Science 92, 548-562.

Derno M, Jentsch W, Schweigel M, Kuhla S, Metges CC and Matthes HD 2005. Measurements of heat production for estimation of maintenance energy requirements of Hereford steers. Journal of Animal Science 83, 2590-2597.

Després G, Veissier I and Boissy A 2002. Effect of autonomic blockers on heart period variability in calves: Evaluation of the sympatho-vagal balance. Physiological Research 51, 347-353.

Freetly HC, Nienaber JA and Brown-Brandl T 2006. Changes in heat production by mature cows after changes in feeding level. Journal of Animal Science 84, 1429-1438.

Fröhli D and Blum JW 1988. Effects of fasting on blood plasma levels, metabolism and metabolic effects of epinephrine and norepinephrine in steers. Acta Endocrinologica 118, 254-259.

Gross JJ, van Dorland HA, Bruckmaier RM and Schwarz FJ. 2011. Performance and metabolic profile of dairy cows during a lactational and deliberately induced negative energy balance with subsequent realimentation. Journal of Dairy Science 94,1820-1830.

Gygax L, Neuffer I, Kaufmann C, Hauser R and Wechsler B 2008. Restlessness behaviour, heart rate and heart-rate variability of dairy cows milked in two types of automatic milking systems and auto-tandem milking parlours. Applied Animal Behaviour Science 109,167-179.

Hagen K, Langbein J, Schmied C, Lexer D and Waiblinger S 2005. Heart rate variability in dairy cows-influences of breed and milking system. Physiology & Behavior 85, 195-204.

Kataoka N, Hioki H, Kaneko T and Nakamura K 2014. Psychological stress activates a dorsomedial hypothalamus-medullary raphe circuit driving brown adipose tissue thermogenesis and hyperthermia. Cell Metabolism 20, 346-358.

Kennedy J, Dillon P, Delaby L, Faverdin P, Stakelum G and Rath M 2003. Effect of genetic merit and concentrate supplementation on grass intake and milk production with Holstein Friesian dairy cows. Journal of Dairy Science 86, 610-621.

Kézér FL, Kovács L, Jurkovich V, Szenci 0 and Tözsér J 2014. Heart rate variability as non-invasive measure of stress in caflle—field studies on Hungarian dairy herds. Hungarian Agricultural Research 4, 33-38.

Krapalis AF, Reiter J, Machleidt F, Iwen KA, Dodt C, Lehnert H and Sayk F 2012. Ghrelin modulates baroreflex-regulation of sympathetic vasomotor tone in healthy humans. American Journal Physiology Regulatory Integrative Comparative Physiology 302, R1305-R1312.

Lambert E, Lambert G, Ika-Sari C, Dawood T, Lee K, Chopra R, Straznicky N, Eikelis N, Drew S, Tilbrook A, Dixon J, Esler M and Schlaich MP 2011. Ghrelin modulates sympathetic nervous system activity and stress response in lean and overweight men. Hypertension 58, 43-50.

Marwan N, Carmen Romano M, Thiel M and Kurths J 2007. Recurrence plots for the analysis of complex systems. Physics Reports 438,237-329.

Matsumura K, Tsuchihashi T, Fujii K, Abe I and Iida M 2002. Central ghrelin modulates sympathetic activity in conscious rabbits. Hypertension 40, 694-699.

Mills SE, and Jenny BF 1979. Effects of high concentrate feeding and fasting on plasma glucocorticoids in dairy heifers. Journal of Animal Science 48, 961-969.

Mohr E, Langbein J and Nümberg G 2002. Heart rate variability: a noninvasive approach to measure stress in calves and cows. Physiology & Behavior 75, 251-259.

Mudron P, Rehage J, Sallmann HP, Höltershinken M and Scholz H 2005. Stress response in dairy cows related to blood glucose. Acta Veterinaria Brno 74, 37-42.

Samuelsson B, Uvnäs-Moberg K, Gorewit RC and Svennersten-Sjaunja K 1996. Profiles of the hormones somatostatin, gastrin, CCK, prolactin, growth hormone and cortisol. II. In dairy cows that are milked during food deprivation. Livestock Production Science 46, 57-64.

Schäff C, Bömer S, Hacke S, Kautzsch U, Albrecht D, Hammon HM, Röntgen M and Kuhla B. 2012. Increased anaplerosis, TCA cycling and oxidative phosphorylation in the liver of dairy cows with intensive body fat mobilization during early lactation. Journal of Proteome Research 11, 5503-5514.

Schrama JW, Roefs JP, Gorssen J, Heetkamp MJ and Verstegen MW. 1995. Alteration of heat production in young calves in relation to posture. Journal of Animal Science. 73, 2254-2262.

Stewart M, Stafford KJ, Dowling SK, Schaefer AL and Webster JR 2008. Eye temperature and heart rate variability of calves disbudded with or without local anaesthetic. Physiology & Behavior 93: 789-797.

Task Force of the European Society of Cardiology and The North American Society for Pacing and Electrophysiology 1996. Heart Rate Variability: Standards of measurement, physiological interpretation, and clinical use. European Heart Journal 17, 354-381.

ThidarMyint H, Yoshida H, Ito T and Kuwayama H 2006. Dose-dependent response of plasma ghrelin and growth hormone concentrations to bovine ghrelin in Holstein heifers. Journal of Endocrinology 189, 655-664.

Thun R, Eggenberger E, Zerobin K, Luscher T and Vetter W 1981. Twenty-four-hour secretory pattern of cortisol in the bull: evidence of episodic secretion and circadian rhythm. Endocrinology 109, 2208-2212.

Turbill C, Ruf T, Mang T and Arnold W 2011. Regulation of heart rate and rumen temperature in red deer: effects of season and food intake. The Journal of Experimental Biology 214, 963-970.

(56) References Cited

OTHER PUBLICATIONS

Vinkers CH, Penning R, Ebbens MM, Hellhammer J, Verster JC, Kalkman CJ and Olivier B 2010. Stress-induced hyperthermia in translational stress research. The Open Pharmacology Journal 4, 285-290.

Weber C, Hametner C, Tuchscherer A, Losand B, Kanitz E, Otten W, Singh SP, Bruckmaier RM, Becker F, Kanitz W and Hammon HM 2013. Variation in fat mobilization during early lactation differently affects feed intake, body condition, and lipid and glucose metabolism in high-yielding dairy cows. Journal Dairy Science 96, 1-16.

Wertz-Lutz A E, Knight TJ, Pritchard RH, Daniel JA, Clapper JA, Smart AJ, Trenkle A and Beitz, DC 2006. Circulating ghrelin concentrations fluctuate relative to nutritional status and influence feeding behavior in cattle. Journal of Animal Science 84, 3285-3300.

Willett LB, and Erb RE 1972. Short term changes in plasma corticoids in dairy cattle. Journal of Animal Science 34, 103-111.

Yang CCH, Chao TC, Kuo TBJ, Yin CS and Chen HI 2000. Preeclamptic pregnancy is associated with increased sympathetic and decreased parasympathetic control of HR. American Journal of Physiology Heart and Circulation Physiology 278, H1269-H1273.

Young JB and Landsberg L 1977. Suppression of sympathetic nervous system during fasting. Science 196, 1473-1475.

International Search Report and Written Opinion for International Patent Application No. PCT/EP2018/075627, dated Oct. 24, 2018, 14 pages.

* cited by examiner

METHOD FOR IDENTIFYING A FARM ANIMAL HAVING AN IMPAIRMENT OF REGULATIVE CAPACITY IN RESPONSE TO METABOLIC STRESS

CROSS-REFERENCE TO RELATED APPLICATIONS

This application is a U.S. National Stage application of International Patent Application No. PCT/EP2018/075627, filed Sep. 21, 2018, which claims the benefit of priority to European Patent Application No. 17192564.7, filed Sep. 22, 2017, the entire contents of each of which are hereby incorporated by reference herein.

BACKGROUND

High performance cattle breeds like German Holstein have been selected for improved milk production and thereby also for high ad libitum feed intake and metabolic rates (Kennedy et al., 2003). On the other hand, dairy cows experience distinct metabolic stress during periods of high metabolic load and inadequate energy/fuel availability leading to a negative energy balance, e.g., as a result of infectious or metabolic/digestive disorders, during heat stress, and in particular during the transition period around parturition (Gross et al., 2011). Sub-clinical disorders of the energy metabolism facilitate failure of homeorhetic and homeostatic adaptations resulting in health problems and reduced performance (Mudron et al., 2005).

Until now various metabolites (i.e., non-esterified fatty acids; NEFA, beta-hydroxybutyrate; BHBA, glucose, lactate) are commonly used to characterize a situation of metabolic stress. In addition, the plasma level of cortisol and the heart rate (HR) are applied to assess a general stress response.

The autonomic nervous system (ANS) plays a predominant role in regulating the adaptive response to inadequate energy and/or fuel availability and the resulting metabolic stress (Chilliard et al., 1998; Fröhli and Blum, 1988). Particularly, the ANS influences the metabolic rate in organs such as heart, liver, and gastrointestinal tract. The sympathetic nervous system (SNS) activity in a variety of tissues/organs is increased in conjunction with high feeding levels and is decreased during starvation (Fröhli and Blum, 1988). Also, the SNS and epinephrine are mainly involved in control of protein kinase A-mediated lipolysis during periods of negative energy balance (NEB) (Chilliard et al., 1998). Together with the adrenocortical axis and behavioral adaptations, the sympathetic nervous system belongs to the main mediators of the stress response (Mudron et al, 2005). Different reactivity/activity of the ANS might thus explain part of the considerable variation in the ability of high-yielding dairy cows to adapt successfully to the metabolic load during pregnancy and onset of lactation. If so, parameters linked to ANS activity and sympatho-vagal balance could be possible early markers of metabolic stress that can be used to predict cows with compromised regulatory capacity.

Linear and non-linear indices of heart rate variability (HRV) have been identified as non-invasive quantitative markers of autonomic activity and of stress (Gygax et al, 2008; Hagen et al., 2005; Mohr et al., 2002). The advantage of HRV over traditional measurement of heart rate (HR), body temperature (BT) or hormone concentrations is its better reflection of the status of the central nervous regulations and of the individual capacity to respond to environmental demands (Task Force, 1996). In cattle HRV analysis has been used to determine stressful effects of high temperature, insect harassment and diarrhea (Mohr et al., 2002), of automatic or conventional milking systems (Gygax et al., 2008; Hagen et al., 2005; Kézér et al. 2014), and of transrectal examination of lactating and dry dairy cows (Kézér et al. 2014). However, there is so far no information on changes of sympathetic and, in particular, of parasympathetic activity pattern in pregnant, high-yielding dairy cows experiencing a defined metabolic load.

SUMMARY

There is an urgent need for predictive markers as well as methods to identify animals at risk and to select animals having a high adaptability and robustness. Thus, the objective underlying the present invention was the provision of a method for identifying a farm animal having an impairment of regulative capacity in response to metabolic stress.

DETAILED DESCRIPTION

Figure 1:
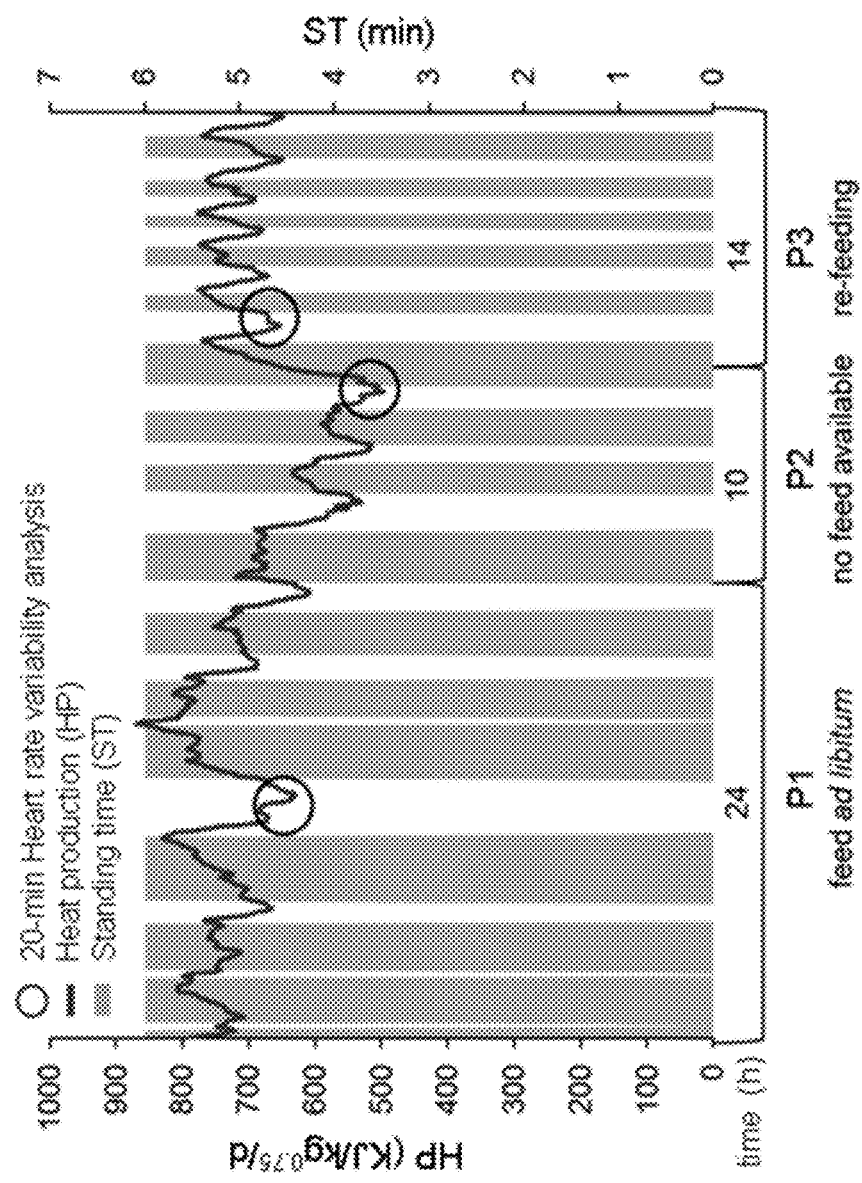
FIG. 1 shows time schedule and experimental design. From one cow representative 48 h original recordings of heat production (HP) and of standing-lying behaviour are also shown. Standing periods (ST) are displayed by grey coloured columns and the right y-axis labelling gives the standing time per 6-min measuring interval in min; 0 min=lying position. The 20-min time periods selected for heart rate variability analysis have been encircled.

According to the present invention, it was found that this object can be solved by a method for identifying a farm animal having an impairment of regulative capacity in response to metabolic stress comprising:
a) assessing the value of the nonlinear domain heart rate variability component $L_{MAX}$ of a farm animal based on a heart beat interval data set obtained for said farm animal;
b) comparing the value of $L_{MAX}$ assessed according to (a) with a species specific threshold of $L_{MAX}$, whereby a farm animal having an impairment of regulative capacity will be identified.

The method is an ex vivo method carried out on an existing dataset of heart beat interval data of a farm animal which does not require any physical interaction with said farm animal. Heart rate (HR) and heart beat interval (Interbeat interval, IBI, R-R interval) data are routinely determined for farm animals, for example, by using Polar Equine systems such as the Polar Equine RS800CX monitor, a fixing belt for large animals (German utility model DE 20 2012 100 735.5) and the equine belt with transmitters and two integrated electrodes (WearLink® W.I.N.D., Polar Electro Oy, Finland). After measurement, the data are routinely transferred to a computer (Polar IrDA USB-Adapter W.I.N.D.). Normally, these data sets are used—preferably after several correction steps—for the determination of HRV parameters of the farm animals in the time, frequency, and nonlinear domains. Due to routine monitoring of farm animals, data sets are available for different feeding periods. Preferably, heart beat interval data sets used according to a) are heart beat interval data of a feed-ad-libitum-period.

$L_{MAX}$ is a HRV indice based on a Lorenz plot (LP), wherein each R-R interval of a data set is plotted against its preceding neighbor. $L_{MAX}$ is defined as the maximal length of the LP shape projection on the bisector. Regarding further details of indices of HRV and their determination, reference is made to Mohr et al. 2002.

The farm animal is preferably selected from the group of species consisting of horse, cow, pig and goat, and is more preferably a cow, more preferably a dairy cow.

In a preferred embodiment, the method further comprises:
c) identifying the farm animal having an impairment of regulative capacity in response to metabolic stress by its value of $L_{MAX}$ being below the species specific threshold.

According to a preferred embodiment, the species specific threshold of $L_{MAX}$ according to (b) is determined based on
  values of the nonlinear domain heart rate variability component $L_{MAX}$ of at least two farm animals of the species to be assessed based on heart beat interval data sets obtained for said farm animals from a feed-ad-libitum-period ($L_{MAX\ ad\ libitum}$);
  values of the high frequency domain parameter of heart rate variability (HF) of the at least two farm animals of the species to be assessed based on heart beat interval data sets obtained for said farm animals from a feed-ad-libitum-period ($HF_{ad\ libitum}$), preferably from the same feed-ad-libitum-period as used for $L_{MAX\ ad\ libitum}$; and
  values of the high frequency domain parameter of heart rate variability (HF) of the at least two farm animals of the species to be assessed based on heart beat interval data sets obtained for said farm animals from a fasting-period ($HF_{fasting}$).

According to a more preferred embodiment, the species specific threshold of $L_{MAX}$ according to (b) is determined by a method comprising:
i) determining the values of the nonlinear domain heart rate variability component $L_{MAX}$ of at least two farm animals of the species to be assessed based on heart beat interval data sets obtained for said farm animals from a feed-ad-libitum-period ($L_{MAX\ ad\ libitum}$);
ii) determining the values of the high frequency domain parameter of heart rate variability (HF) of the same at least two farm animals as in (i) based on heart beat interval data set obtained for said farm animals from a feed-ad-libitum-period ($HF_{ad\ libitum}$);
iii) determining the values of the high frequency domain parameter of heart rate variability (HF) of the same at least two farm animals as in (i) based on heart beat interval data sets obtained for said farm animals from a fasting-period ($HF_{fasting}$).

According to a more preferred embodiment, the method for determining the species specific threshold of $L_{MAX}$ according to (b) further comprises:
iv) determining the difference between $HF_{ad\ libitum}$ and $HF_{fasting}$ ($\Delta HF$) for each of the at least two farm animals;
v) linear regression $\Delta HF$ versus $L_{MAX\ ad\ libitum}$.

$HF_{ad\ libitum}$, $HF_{fasting}$ and $L_{MAX\ ad\ libitum}$ of least two farm animals are necessary to know in order to carry out the linear regression according to v). Preferably, the data of more than two farm animals, more preferably of at least ten farm animals, more preferably of at least twenty farm animals are used.

According to a more preferred embodiment, the method for determining the species specific threshold of $L_{MAX}$ according to (b) further comprises:
vi) determining the species specific threshold of $L_{MAX}$ in that the value of $L_{MAX\ ad\ libitum}$ corresponding to $\Delta HF=$zero in the linear regression according to v) represents the species specific threshold of $L_{MAX}$.

Preferably, for dairy cows, the species specific threshold of $L_{MAX}$ is in the range of from 200 to 300, more preferred in the range of from 220 to 280, more preferred in the range of from 250 to 270, more preferred in the range of from 255 to 265, more preferred 258.

Below, the work done by the inventors in order to arrive at the method outlined above is described in more detail:

Autonomic regulation and stress level of dry, pregnant, high yielding dairy cows in response to a 10-hour feed deprivation by using heart rate variability (HRV) analysis were investigated. A wide range of HRV indices before, during and after a 10-hour feed removal was investigated. The aims of the experimental work have been (1) to develop a procedure suitable to identify group-specific or inter-individual differences in the cow's metabolic stress level and regulatory capacity in response to a 10-h food removal, (2) to identify specific HRV indices reflecting this different status already under control conditions (ad libitum feeding) and (3) can be used as predictive markers.

Material and Methods

Cows and Diet

Experiments were performed with 10 multiparous dried-off German Holstein cows (4 to 6 years old, mean body mass: 726±56 kg) born and raised at the farm of Griepentrog KG (Steinhagen, Germany), during week four ante-partum (ap). Two of the cows (number 3 and 10) were halfsiblings having the same father. All cows had a milk yield of ≥10,000 kg/305 days during the prior lactation and had been dried off at 7 weeks before expected calving. Cows were fed a far-off total mixed ration (TMR) twice daily at approximately 07:00 and 15:00 and had free access to water. The TMR was formulated to meet the nutrient recommendations of the German Society for Nutrition Physiology (2001), and its ingredients and chemical composition are given in table 1.

TABLE 1

Ingredients and chemical composition of the total mixed ration.

Components

Ingredient, g/kg of DM

| | |
|---|---|
| Grass silage | 749.0 |
| Corn silage | 29.0 |
| Barley straw | 114.0 |
| Hay | 95.0 |
| Concentrate[1] | 1.3 |

TABLE 1-continued

Ingredients and chemical composition of the total mixed ration.

| Components | |
| --- | --- |
| Molassed sugar beet pulp[2] | 4.1 |
| Mineral feed[3] | 7.7 |
| Chemical Analysis | |
| Utilizable crude protein, g/kg of DM | 128.0 |
| Crude fat, g/kg of DM | 38.0 |
| $NE_L$, MJ/kg of DM | 5.9 |
| NDF g/kg of DM | 335.0 |
| ADF g/kg of DM | 189.0 |

[1]Concentrate MF 2000 (Vollkraft Mischfutterwerke GmbH, Güstrow, Germany): 33% extracted soy meal, 20% corn, 17% wheat gluten, 13% wheat, 8% extracted rapeseed meal, 5% sugar beet pulp, 2% sodium hydrogen carbonate, 1.3% calcium carbonate, 0.2% sodium chloride, 8.0 MJ of NEL/kg of DM, 204 g of utilizable protein/kg of DM.
[2]Molassed sugar beet pulp (Arp, Thordsen, Rautenberg GmbH & Co KG, Sollerupmühle, Germany): minerals, 7.3 MJ of NEL/kg of DM, 153 g of utilizable protein/kg of DM.
[3]Rinderstolz 9235 far-off (Salvana Tiernahrung GmbH, Sparrieshoop, Germany): 75% crude ash, 4.5% calcium, 6% phosphorus, 10% sodium, 12% magnesium, vitamins Experimental Design During weeks −7 to −5 ap, cows were adapted to handling and to staying in respiration chambers (see indirect calorimetry) in which the experimental trials were performed. Habituation (criteria: eating, drinking, ruminating, lying down, body temperature) was performed at least three times and the duration of stay was increased from 1 hour on day 1 to 3-4 hours on day 4. No animal needs longer than 4 days to habituate. At the same time points cows were adapted to wear a fixing belt (criteria: scrubbing, licking, looking to the belt, restlessness), which was tied around the thorax behind the forelegs and is needed for HRV measurements.

The experimental trial was started one day after the cows were transferred to the respiration chambers. HR and inter-beat intervals (IBI) computed from the intervals between consecutive R-peaks were continuously measured for 48 h starting at 06:30. In addition, $O_2$ consumption, $CO_2$ and $CH_4$ production, food intake, and physical activity including standing-lying behaviour were monitored. After 24 h of ad libitum feeding (period 1; P1), feed was removed for 10 h (period 2, P2) to challenge the energy metabolism of the cows. Thereafter, the cows were provided with food ad libitum for a 14-hour (16:30 to 06:30) period of re-feeding (period 3, P3). The time course and the experimental periods (P1-P3) of the trial are shown in FIG. 1. The cows were weighed immediately before entering and after leaving the chambers on balances in front of the chambers. The continuous measurements were interrupted for 0.5 h (06:30 to 07:00) on day two to clean the chambers and to measure their body temperature (BT). The latter was also measured after the second feeding (15:00) during P1 and P3 and at 16:30 during P2.

HRV Measurement and Analysis

HR and R-R interval data were taken noninvasively by using the Polar Equine RS800CX monitor, a newly developed fixing belt for large animals (FBN utility model, case number: DE 20 2012 100 735.5) and the equine belt with transmitters and two integrated electrodes (WearLink® W.I.N.D., Polar Electro Oy, Finland). A few days before the experimental period, the electrode site, an area of about 10×15 cm localized directly behind the left shoulder of the cow, was shaved. To optimize conductivity, the electrodes were made moist before the measuring belt with integrated electrodes has placed on this region.

After measurement, the data were transferred from the monitor to a computer (Polar IrDA USB-Adapter W.I.N.D.), and relevant data sets from the three experimental periods (P1-P3) were selected according to heat production (HP). Moreover, in order to minimize the additional effects of physical activity, only those data sets that were recorded during periods when the cows were lying down were taken into consideration. During P1, an interval after the last meal characterized by a stable maximum HP was chosen and compared with an interval with consistently low HP occurring at the end of P2. In P3, a rapid increase of HP was observed after re-submission of food. For data analysis an interval was selected were HP has stabilized. FIG. 1 shows typical original traces of HP and standing-lying behaviour obtained from an individual cow. In addition, the periods chosen for HRV analysis are given.

Subsequently, by using the software "Polar ProTrainer 5 Equine Edition" Version 5.35.161 (Polar Electro Oy, Finland), an automatic correction for artefacts was performed. Only data sets that were at least 20 min long and had a corrected fault rate of less than 10% for each 5-min interval were included in the analysis (Mohr et al., 2002).

Corrected 20-min data sets were converted into text files and saved, and HRV parameters in the time, frequency, and nonlinear domains were calculated (Table 2) from an adjacent 5-min window that moved over the data set by use of Kubios HRV software Version 2.0.

TABLE 2

Glossary for time domain, frequency domain, and nonlinear domain measures of heart rate variability (Borell, von et al., 2007; Mohr et al., 2002)

| | Parameter | Physiological meaning |
| --- | --- | --- |
| Time domain | Hart rate; HR (beats per minute, bpm) Frequency of heart beats | Joint activity of vagus and sympathicus |
| | Interbeat interval, IBI, R-R interval (ms) Time interval between succeeding heart beats | Joint activity of vagus and sympathicus |
| | RMSSD (ms) Standard deviation of differences between successive R-R intervals | vagally mediated changes in the sympatho-vagal balance, short-term variability |
| | SDNN (ms) Standard deviation of all RR intervals | Overall variability present at the time of recording, long-term variability |
| | HRV triangular index; $HRV_{index}$ Integral of all R-R intervals divided by the height of the histogram of all R-R intervals | Joint activity of vagus and sympathicus |
| Frequency domain | Low frequency; LF [n.u.] Normalized power in the low frequency band ranging from 0.0133 to 0.2 Hz | Joint activity of vagus and sympathicus; results primary from activity of sympathetic neurons, effect via vasomotoric activity |
| | High frequency; HF [n.u.] | Vagal activity, respiratory sinus arrhytmia |

TABLE 2-continued

Glossary for time domain, frequency domain, and nonlinear domain measures of heart rate variability (Borell, von et al., 2007; Mohr et al., 2002)

| | Parameter | Physiological meaning |
|---|---|---|
| | Normalized power in the high frequency band ranging from 0.2 to 0.58 Hz | |
| | LF/HF* | Sympatho-vagal balance |
| | Ratio between LF and HF band powers | |
| Nonlinear domain* | Maxline; $L_{MAX}$ | Proportion of deterministic chaos or coincidence in a system |
| | Longest diagonal line segment of consecutive recurrence points | |
| | Percentage of recurrence; % REC points in the whole triangular area; vector repetition in the multidimensional space | Flexibility of a system (quantitative) |
| | Shannon Entropy; ShanEn deterministic line length distribution | Complexity or irregularity of HRV |

*Quantitative parameters derived from recurrence plots by non-linear mathematical analysis of HRV (Recurrence Quantification Analysis, RQA)

The dissimilar respiratory frequencies in cattle and humans were taken into consideration by setting the limits of the high frequency (HF), low frequency (LF), and very low frequencies (VLF) bands to 0.2 Hz (lower limit) and 0.58 Hz (upper limit), 0.0133 and 0.2 Hz, and 0.0033 and 0.0133 Hz, respectively (Borell, von et al., 2007). Recurrence quantification analysis (RQA) was used to calculate nonlinear parameters of HRV with the Kubios software Version 2.0. RQA was performed with an embedding dimension m=10, lag of 1, and a threshold distance (radius) r of $\sqrt{m}$ SD, with SD as the standard deviation of the R-R time series.

Indirect Calorimetry and Behavioural Data

Gas exchange of the cows was measured continuously at 6-min intervals in climate-controlled (15° C., 70% humidity) open-circuit respiration chambers with a volume of 16 m³. All chambers (dimension 4×2×2 m) contained a stanchion allowing the individual animal to stand or lie down. Standing and lying times of the cows were registered by a photoelectric switch (SA1E, idec Elektrotechnik GmbH, Hamburg, Germany). Other physical activity was detected by a modified infrared-based motion detector (IS 120, STEINEL, Herzebrock-Klarholz, Germany) converting movements of the animal into impulses.

Feed intake was assessed automatically by measuring feed disappearance from the chamber feed bin (maximum capacity: 40 kg organic substance) via a scale connected to an electronic registration device (PAARI, Erfurt, Germany).

Gas samples were passed through infrared absorption based analysers (UNOR 610, MAIHAK AG, Hamburg, Germany) for the determination of $CO_2$ and $CH_4$ content and through a paramagnetic analyser (OXYGOR 610, MAIHAK, Hamburg, Germany) for measurement of $O_2$ content. Based on these data, HP was estimated according to Brouwer (1965): HP (KJ)=16.18 $O_2$ (l)+5.02 $CO_2$ (l)−2.17 $CH_4$ (l)−5.99 N (g).

All measured variables (gas concentrations for $O_2$, $CO_2$, and $CH_4$, air flow rate, feed disappearance from the feed bin, temperature and relative humidity in and behind the chamber, standing and lying time, activity counts, air pressure) were sent to an acquisition system (Simatic, Siemens, München, Germany) and collected by purpose-adapted software (WinCC, Version 5.1, SP 2, Siemens, München, Germany). DELPHI-based (Delphi 2007, San Francisco, Calif., USA) software was programmed in our group (Copyright H. Scholze, FBN) to allow for the automatic calculation of HP and collection of all measured data in EXCEL files.

To obtain accurate information on the cows energy status and rumen fermentation activity, the energy balance (EB) and fermentative $CO_2$ ($CO_2$(ferm) for P1, P2 and P3 were calculated from the measured data by using the following equations: EB (KJ)=ME-Intake (KJ)−HP (KJ) and $CO_2$ (ferm) (l)=1.7×$CH_4$ production (l).

Blood Sampling and Analysis

Cows were equipped with indwelling jugular catheters the day before the trial starts. Extension tubing was used to take blood samples from outside the respiration chambers into Fe-Fluoride monovettes (Sarstedt, Germany) and immediately put on ice. Blood samples were centrifuged (2,700 rpm (4,000×g), 4° C.) for 20 min and the supernatants were stored at −80° C. until analysis for NEFA, BHBA, total ghrelin, and cortisol. Plasma concentrations of NEFA and BHBA were measured by routine analysis (Cobas Mira, Clinic for Cattle, Stiftung Tierärztliche Hochschule Hannover, Hannover, Germany) using kits from Wako Chemicals (NEFA kit 434-91795) and Randox Laboratories (BHBA kit RB 998), respectively. Total ghrelin (acyl+desacyl ghrelin) was determined in 400-µl freeze-dried plasma samples by using the RIA method described previously by ThidarMyint et al. (2006). Plasma cortisol concentrations were determined by radioimmunoassay at the Veterinary Physiology, Vetsuisse Faculty, University of Bern as described previously by Thun et al (1981).

Statistical Analysis

The statistical analyses were carried out by using SAS software, Version 9.4 for Windows. Copyright, SAS Institute Inc., Cary, N.C., USA.

Differences of the HRV variables (Table 3) and of parameters related to the energy, nutrient and activity status (Table 4) between various periods (P1, P2 and P3) were analysed by one way repeated measurement ANOVA.

TABLE 3

Heart rate variability indices determined for cows under control conditions (P1 = ad libitum feeding) and during fasting (P2) or re-feeding (P3 = food ad libitum).

| | Parameter | Period | LSM | SE | Min | Max |
|---|---|---|---|---|---|---|
| Time domain | HR [bpm] | P1 | 71.7$^a$ | 1.5 | 59.3 | 80.9 |
| | | P2 | 60.9$^b$ | 1.6 | 52.1 | 68.5 |
| | | P3 | 72.7$^a$ | 1.4 | 62.2 | 78.9 |
| | RR [ms] | P1 | 844.0$^a$ | 19.0 | 744.0 | 1014.0 |
| | | P2 | 993.0$^b$ | 26.0 | 878.0 | 1154.0 |
| | | P3 | 832.0$^a$ | 17.0 | 762.0 | 966.0 |
| | RMSSD [ms] | P1 | 12.8 | 2.2 | 4.9 | 25.7 |
| | | P2 | 16.5 | 2.0 | 6.6 | 25.4 |
| | | P3 | 12.4 | 2.1 | 5.2 | 22.8 |

TABLE 3-continued

Heart rate variability indices determined for cows under control conditions (P1 = ad libitum feeding) and during fasting (P2) or re-feeding (P3 = food ad libitum).

| | Parameter | Period | LSM | SE | Min | Max |
|---|---|---|---|---|---|---|
| | SDNN [ms] | P1 | 30.5 | 3.0 | 20.4 | 53.8 |
| | | P2 | 41.9 | 4.6 | 23.2 | 65.1 |
| | | P3 | 37.8 | 3.7 | 23.6 | 62.4 |
| | $HRV_{index}$ | P1 | 6.4 | 0.5 | 3.9 | 10.7 |
| | | P2 | 7.5 | 0.7 | 4.6 | 10.3 |
| | | P3 | 6.7 | 0.6 | 4.4 | 10.2 |
| Frequency domain | LF [n.u.] | P1 | 90.9 | 2.6 | 67.0 | 98.9 |
| | | P2 | 89.2 | 2.0 | 77.0 | 99.3 |
| | | P3 | 92.4 | 2.5 | 76.2 | 99.5 |
| | HF [n.u.] | P1 | 9.1 | 2.6 | 1.1 | 33.0 |
| | | P2 | 10.8 | 2.0 | 0.7 | 23.0 |
| | | P3 | 7.6 | 2.5 | 0.5 | 23.8 |
| | LF/HF* | P1 | 31.7 | 10.3 | 2.1 | 98.1 |
| | | P2 | 34.8 | 15.4 | 3.5 | 152.0 |
| | | P3 | 44.8 | 20.0 | 3.4 | 208.0 |
| Nonlinear domain | $L_{MAX}$ | P1 | 277.0$^{ab}$ | 26.0 | 41.0 | 394.0 |
| | | P2 | 236.0$^{a}$ | 17.0 | 160.0 | 304.0 |
| | | P3 | 313.0$^{b}$ | 29.0 | 68.0 | 384.0 |
| | % REC | P1 | 46.5 | 3.4 | 20.0 | 57.7 |
| | | P2 | 51.0 | 1.9 | 40.0 | 66.3 |
| | | P3 | 52.1 | 2.8 | 39.3 | 62.5 |
| | ShanEn | P1 | 3.7 | 0.1 | 2.6 | 4.2 |
| | | P2 | 3.8 | 0.1 | 3.4 | 4.2 |
| | | P3 | 3.8 | 0.1 | 3.2 | 4.4 |

*LF/HF has been calculated from the non-normalized values of HF and LF (not shown).
P1 = control (ad libitum feeding), P2 = fasting, and P3 = re-feeding (food ad libitum).
Min = Minimum value; Max = Maximum value; Data are given as LSM ± SE; N = 10.
$^{a,b,c}$Significant differences between periods (P < 0.05).

TABLE 4

Response of parameters related to the energy, nutrient and activity status to a 10-hours fasting (P2) and 14-hours re-feeding (P3) period.

| Parameter | Units | Period | LSM | SE | Min | Max |
|---|---|---|---|---|---|---|
| BT | ° C. | P1 | 38.42 | 0.09 | 38.00 | 39.16 |
| | | P2 | 38.46 | 0.06 | 38.10 | 39.60 |
| | | P3 | 38.39 | 0.09 | 38.10 | 39.10 |
| Cortisol | nM/l | P1 | 5.54 | 0.30 | 3.98 | 9.77 |
| | | P2 | 5.67 | 0.45 | 3.56 | 17.64 |
| | | P3 | 6.36 | 0.78 | 1.56 | 9.33 |
| Cortisol Peak | nM/l | End of P2 | 5.99 | 0.81 | 3.52 | 18.42 |
| HP | KJ/ kg$^{0.75}$/d | P1 | 750.56$^{a}$ | 48.09 | 551.17 | 1177.07 |
| | | P2 | 620.58$^{b}$ | 39.81 | 463.72 | 1075.35 |
| | | P3 | 765.12$^{a}$ | 47.43 | 566.30 | 1207.29 |
| EB | KJ/ kg$^{0.75}$/d | P1 | −22.78$^{a}$ | 45.46 | −1060.40 | 186.68 |
| | | P2 | −615.20$^{b}$ | 41.52 | −2292.54 | −462.30 |
| | | P3 | 339.72$^{c}$ | 83.30 | −382.24 | 851.28 |
| DMI | kg/h | P1 | 0.44$^{a}$ | 0.04 | 0.30 | 1.40 |
| | | P2 | | | | |
| | | P3 | 0.65$^{b}$ | 0.06 | 0.49 | 1.33 |
| WI | l/d | P1 | 25.95$^{a}$ | 3.82 | 12.00 | 99.00 |
| | | P2 | 3.98$^{b}$ | 1.17 | 1.00 | 31.00 |
| | | P3 | 24.07$^{a}$ | 3.21 | 14.00 | 87.00 |
| CO$_2$ (ferm) | l/h | P1 | 21.87$^{a}$ | 1.54 | 12.59 | 38.01 |
| | | P2 | 12.65$^{b}$ | 0.89 | 9.06 | 20.30 |
| | | P3 | 22.27$^{a}$ | 1.28 | 15.05 | 40.00 |
| Activity | counts/h | P1 | 10818.00$^{a}$ | 1342.00 | 4474.00 | 21034.00 |
| | | P2 | 7065.00$^{b}$ | 833.00 | 2122.00 | 15803.00 |
| | | P3 | 11583.00$^{a}$ | 1957.00 | 3468.00 | 21359.00 |
| Standing/ Lying | | P1 | 1.60$^{a}$ | 0.23 | 0.55 | 3.36 |
| | | P2 | 0.91$^{b}$ | 0.18 | 0.22 | 1.60 |
| | | P3 | 1.87$^{a}$ | 0.40 | 0.75 | 4.79 |
| Ghrelin total | ng/ml | P1 | 1.99$^{a}$ | 0.57 | 0.32 | 5.04 |
| | | P2 | 5.30$^{b}$ | 0.89 | 0.89 | 12.69 |
| | | P3 | 1.80$^{a}$ | 0.47 | 0.20 | 4.38 |

TABLE 4-continued

Response of parameters related to the energy, nutrient and activity status to a 10-hours fasting (P2) and 14-hours re-feeding (P3) period.

| Parameter | Units | Period | LSM | SE | Min | Max |
|---|---|---|---|---|---|---|
| NEFA | µM/l | P1 | 176.37$^{a}$ | 37.27 | 72.17 | 864.67 |
| | | P2 | 328.00$^{b}$ | 31.08 | 144.94 | 1724.00 |
| | | P3 | 169.65$^{a}$ | 33.52 | 67.2 | 1309.00 |
| BHBA | mM/l | P1 | 0.40 | 0.03 | 0.26 | 2.82 |
| | | P2 | 0.37 | 0.03 | 0.24 | 2.24 |
| | | P3 | 0.43 | 0.05 | 0.24 | 2.29 |

P1 = control (ad libitum feeding), P2 = fasting, and P3 = re-feeding (food ad libitum).
Data are given as LSM ± SE; Min = Minimum value; Max = Maximum value; N = 10.
$^{a,b,c}$Significant differences between periods (P < 0.05).

With the exception of BT, all parameters from table 4 were evaluated as 24 h-means for the ad libitum feeding period (P1: 240 data sets) and as means for the fasting period (P2: 06:30 to 16:30 h, 99 data sets) and for the ad libitum re-feeding period (P3: 16:30 to 06:30, 140 data sets). Data obtained in P2 and P3 were converted into 24-h values.

The response of HF (an indicator of parasympathetic activity) to fasting ($HF_{P1}-HF_{P2}=\Delta HF_{P1-P2}$) was evaluated for individual cows. $HF_{P1}$ is synonymously also called $HF_{ad\ libitum}$, $HF_{P2}$ is synonymously also called $HF_{fasting}$ and $\Delta HF_{P1-P2}$ is synonymously also called simply $\Delta HF$, i.e. $HF_{P1}-HF_{P2}=\Delta HF_{P1-P2}$ can synonymously be expressed as $\Delta HF=HF_{ad\ libitum}-HF_{fasting}$. $\Delta HF_{P1-P2}/\Delta HF$ allows for separation of two groups (HF+ (increase of HF in response to fasting) and HF− (decrease of HF in response to fasting) cf. FIG. 2). Then HRV data were analysed by two-way repeated measurement analysis of variance (ANOVA) with the MIXED procedure of SAS/STAT software. The ANOVA model contained the fixed effects Group (levels: HF+ and HF−) and Period (levels: P1, P2, P3) and the interaction Group * Period. Repeated measurements on the same animal were taken into account by the repeated statement of the MIXED procedure by using an unstructured residual covariance matrix.

In a further analysis the relationship between $\Delta HF_{P1-P2}$ and HR, R-R interval, and $L_{MAX}$ at P1 ($L_{MAX\ ad\ libitum}$) was investigated by linear regression using the REG procedure of SAS/STAT software with the aim to select possible biomarker(s) that predict the sensitivity of individual cows for metabolic stress, and to define a threshold for such biomarker. Of the investigated HRV parameters only $L_{MAX}$ fulfilled the criteria for a possible biomarker and two groups ($<L_{MAX}$ ($L_{MAX}$ lower than threshold in P1: control conditions with feed ad libitum) and $>L_{MAX}$ ($L_{MAX}$ higher than threshold in P1: control conditions with feed ad libitum) cf. FIG. 3A) were defined. After grouping the cows according to the $L_{MAX}$ threshold one way ANOVAs were done for the variables BT, HP, EB, CO$_2$(ferm), dry matter intake (DMI) and water intake (WI), plasma concentrations of NEFA, BHBA, glucose, cortisol, ghrelin (total), and insulin, standing time, activity and milk parameters (energy corrected milk; ECM, milk fat, milk protein, milk lactose and fat/protein quotient) to test the group effect (test for biomarker).

The first ANOVA model contained the fixed effects Group (levels: $<L_{MAX}$ and $>L_{MAX}$) and Day (levels: day 1=P1 and day 2=P2+P3 ante partum, day 3=P1 and day 4=P2+P3 post partum) and the interaction Group * Day (Table 5).

TABLE 5

Prepartal and postpartal <Lmax und >Lmax group differences in parameters related to metabolic status and stress level.

| Parameter | Day | <Lmax LSM | <Lmax SE | >Lmax LSM | >Lmax SE | P value |
|---|---|---|---|---|---|---|
| BT | 1 | 38.53 | 0.16 | 38.30 | 0.11 | n.s |
| (° C.) | 2 | 38.64 | 0.11 | 38.27 | 0.07 | 0.0206 |
| | 3 | 38.92 | 0.15 | 38.63 | 0.15 | n.s |
| | 4 | 38.93 | 0.24 | 38.50 | 0.16 | n.s. |
| Cortisol | 1 | 6.22 | 0.51 | 4.86 | 0.33 | 0.0534 |
| (nM/l) | 2 | 6.07 | 0.75 | 5.27 | 0.49 | n.s. |
| | 3 | 6.60 | 1.10 | 7.23 | 0.72 | n.s. |
| | 4 | 8.75 | 1.78 | 11.17 | 1.16 | n.s. |
| Cortisol Peak | 2 | 6.76 | 1.35 | 5.22 | 0.88 | n.s. |
| (nM/l) | 4 | 8.40 | 1.88 | 15.05 | 1.23 | 0.0200 |
| HP | 1 | 750.12 | 80.12 | 744.80 | 52.45 | n.s. |
| (kJ/kg$^{0.75}$/d) | 2 | 703.75 | 73.23 | 702.02 | 47.94 | n.s. |
| | 3 | 953.54 | 45.45 | 1064.14 | 29.75 | 0.0761 |
| | 4 | 902.22 | 58.51 | 1016.78 | 38.30 | n.s. |
| EB | 1 | −6.07 | 6.32 | 6.80 | 4.14 | n.s. |
| (kJ/kg$^{0.75}$/d) | 2 | −14.20 | 11.69 | −1.25 | 7.66 | n.s. |
| | 3 | −66.98 | 21.22 | −94.17 | 13.89 | n.s. |
| | 4 | −66.77 | 20.04 | −115.60 | 13.12 | 0.0759 |
| Ghrelin | 1 | 2.17 | 0.95 | 1.80 | 0.62 | n.s. |
| ng/ml | 2 | 5.23 | 1.49 | 5.37 | 0.98 | n.s. |
| | 3 | 1.28 | 0.65 | 2.10 | 0.42 | n.s. |
| | 4 | 5.87 | 1.34 | 10.17 | 0.88 | 0.0279 |
| ECM | 3 | 40.59 | 3.88 | 50.14 | 2.54 | 0.0734 |
| kg/d | 4 | 40.93 | 2.20 | 49.86 | 1.44 | 0.0095 |

Day 1/3 (P1) = control (ad libitum feeding) ante partum/post partum, Day 2/4 (P2 + P3) = fasting and re-feeding (food ad libitum) ante partum/post partum.
Data are given as LSM ± SE, N = 16, Significant differences between <Lmax and >Lmax groups (P < 0.05), n.s. = not significant The second ANOVA model contained the fixed effects Group (levels: <$L_{MAX}$ and >$L_{MAX}$) and Week (levels: weeks −5 to −2 ante partum and weeks +2 to +5 post partum) and the interaction Group * Week (Table 6).

TABLE 6

Prepartal and postpartal <Lmax und >Lmax group differences in cows kept under normal housing conditions.

| Parameter | Units | Weeks | <Lmax LSM | <Lmax SE | >Lmax LSM | >Lmax SE | P value |
|---|---|---|---|---|---|---|---|
| Insulin | µg/l | ap | 8.41 | 5.64 | 27.50 | 3.74 | 0.0274 |
| | | pp | 6.86 | 3.04 | 7.67 | 1.99 | n.s. |
| DMI | kg/d | ap | 10.50 | 1.12 | 12.65 | 0.65 | n.s. |
| | | pp | 15.99 | 0.73 | 18.51 | 0.42 | 0.0099 |
| ECM | kg/d | pp | 41.80 | 1.97 | 47.29 | 1.14 | 0.0302 | ap = weeks −5 to −2 ante partum, pp = weeks +5 to +2 post partum, N = 16

Repeated measurements on the same animal were taken into account by the repeated statement of the MIXED procedure by using an unstructured residual covariance.

Least square means (LSM) and their standard errors (SE) were calculated and pairwise tested for each effect in each model by using the Tukey-Kramer procedure for pairwise multiple comparisons. Effects and differences were considered significant if P<0.05.

Results

Response of HR and HRV Indices to a 10-h Feed Deprivation and Subsequent Re-Feeding Table 3 summarizes the effects of the 10-h feed deprivation (P2) and subsequent re-feeding (P3) on HRV indices. The mean HR and the resulting R-R interval were 72±2 beats/min and 844±19 ms, respectively, under control conditions (ad libitum feeding, P1). HR and R-R intervals showed a significant reduction (15±2%) or increase (18±3%) in P2 compared with P1 and returned to baseline levels during P3 (Table 3). During all experimental periods HR was positively correlated with HP (P1: r=0.58, p=0.08; P2: r=0.78, p=0.007; P3: r=0.72, p=0.02). $L_{MAX}$ values were significantly higher during the refeeding period (313±29) compared with P2 (236±17). Over all cows none of the other HRV parameters were significantly influenced by the 10-h feed deprivation.

Characterization of the Energy and Metabolic Status, and the Behavioural Response of the Cows Parameters related to the energy, metabolic and behavioural status of cows are depicted in Table 4 showing significant effects of the 10-h feed deprivation on heat production (HP), energy balance (EB), fermented carbon dioxide ($CO_2$(ferm)), NEFA, total ghrelin, and physical activity. The measured EB was already negative in P1. As expected, compared with P1, the cows EB switched to strongly negative values during P2 and recovered to significantly more positive values during P3. This was accompanied by reductions of HP (18±1%, P<0.05), physical activity (33±3%, P<0.05), standing:lying ratio (40±7%, P<0.05), and production of $CO_2$(ferm) (41±2%, P<0.05) in P2 and recovery of these parameters to ad libitum levels in P3. NEFA plasma concentrations increased 1.8-fold (P<0.05) and total ghrelin concentrations 2.8-fold (P<0.001) during P2 and normalized during P3. A compensatory increase of dry matter intake (DMI) amounting to 48% was seen in P3 compared with P1.

Mean body temperature of cows was 38.4° C. during all feeding periods. In addition, cortisol levels reacted only marginally to the feed removal (P2) or re-feeding (P3).

Analyses of HRV Responses to Feed Removal in Individual Cows

Figure 2:
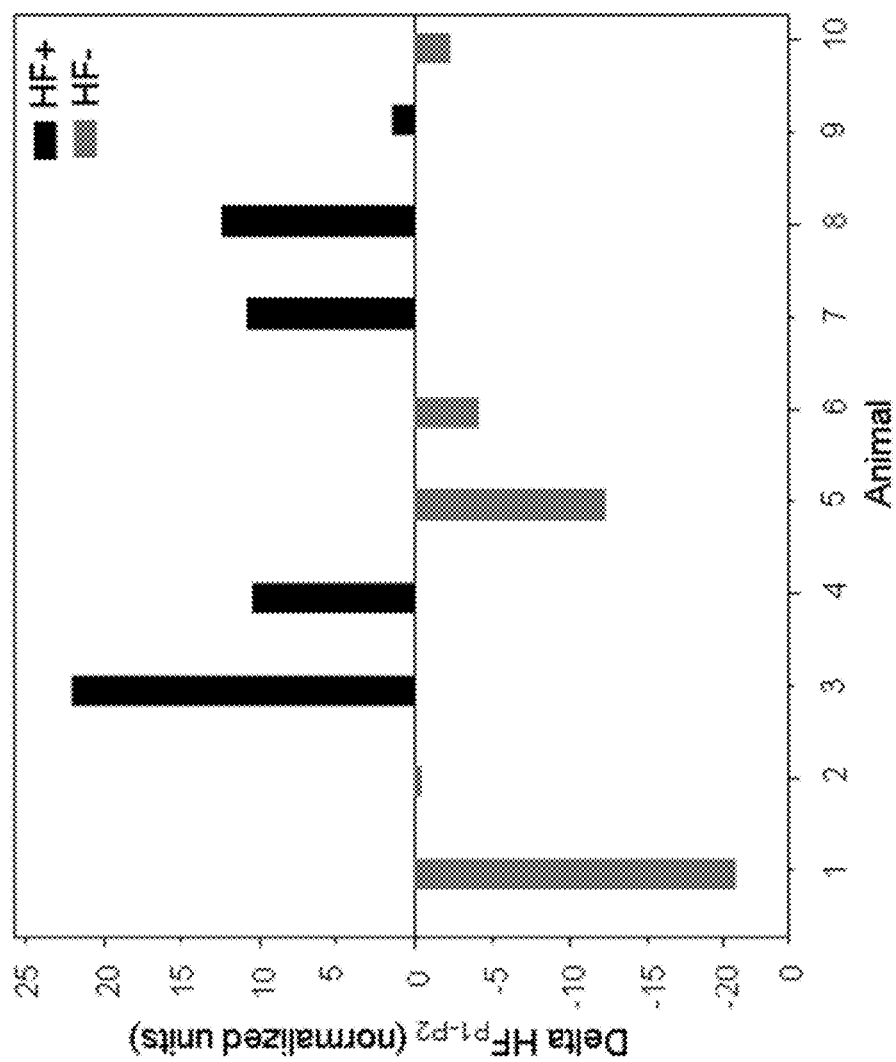
FIG. 2 shows response of the high frequency domain (HF) of heart rate variability to fasting. It mainly reflects the activity of the parasympathetic branch of the autonomic nervous system. The response of HF to fasting (HF during ad libitum feeding (P1) minus HF during fasting (P2)= $\Delta HF_{P1-P2}$) is shown for individual cows. Note the increase in vagal tone ($\Delta HF_{P1-P2}$ increase) in five out of 10 cows (defined as group HF+) and an impaired vagal activation ($\Delta HF_{P1-P2}$ decrease) in another five cows (assigned to group HF−).
Figure 3:
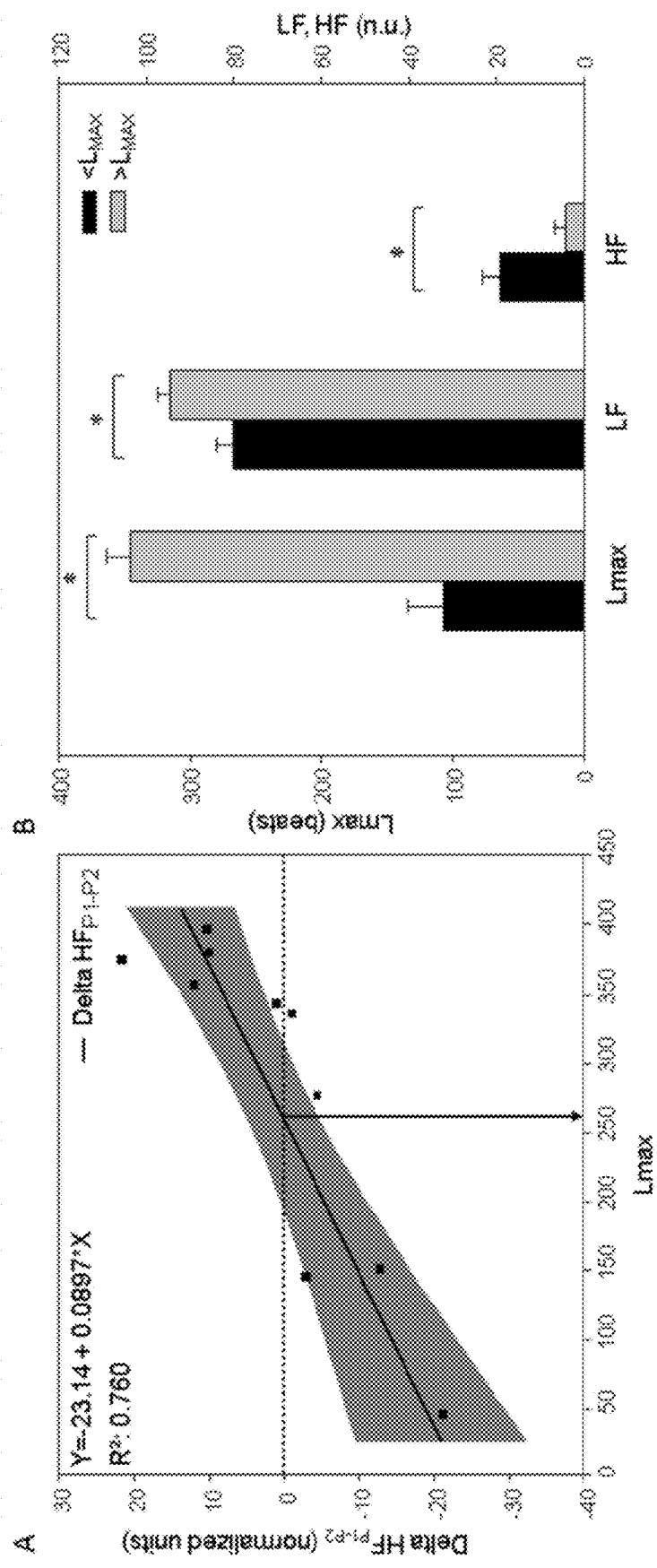
FIG. 3 shows prediction of group differences in autonomic control by the nonlinear domain HRV component Maxline ($L_{MAX}$). A: Regression analysis was performed with $\Delta HF_{P1-P2}$ as depend, and $L_{MAX}$ as independent variable. The obtained regression model ($R^2$=0.76) allows for calculation of a threshold value (TS=258) for $L_{MAX}$ and assignment of cows to groups having $L_{MAX}$ values above ($>L_{MAX}$) or below ($<L_{MAX}$) the TS. B: Under control conditions (P1: ad libitum feeding) cows of the $>L_{MAX}$ (N=7) and $<L_{MAX}$ (N=3) groups differ in LMAX (P<0.001), high-frequency (HF, P<0.002), and low-frequency (LF, P<0.002) components of HRV.

The minimum and maximum values of calculated HRV indices show a wide range (Table 3) pointing to inter-individual differences. Therefore, the behaviour of frequency-domain parameters (HF, LF, LF/HF), known indicators of autonomic control, in response to the 10-h feed deprivation (ΔP1-P2) was evaluated for individual cows allowing for the separation of two groups. As shown in FIG. 2, after feed removal, the power in the HF band which reflects the parasympathetic control increased in five cows (HF+), but in the other five cows, a decrease (HF−) was observed. A reverse response, i.e., a decrease in the HF+ group and an elevation in HF− group, was observed for LF (−12±3% vs. 11±6%) and the LF/HF ratio (−73±11% vs. 500±312%), respectively. Cows retrospectively assigned to these two groups were shown to differ significantly in their HR (HF+: 76±2 bpm, HF−: 68±2.4 bpm), R-R interval (HF+: 796±18 ms, HF−: 892±33 ms) and $L_{MAX}$ (HF+: 357±26, HF−: 187±52) under ad libitum control conditions (P1). Thus, a possible link between these parameters and $ΔHF_{P1-P2}$ was tested by performing regression analysis. The coefficient of determination ($R^2$) was low for HR (0.372) and R-R interval (0.325). However, a regression model with $L_{MAX}$ as independent variable reveal an $R^2$ of 0.76 (FIG. 3A), suggesting that it explains the variation in $ΔHF_{P1-P2}$ to a high extent. From this regression model a threshold (TS=0=−23.14+0.0897*$L_{MAX}$) for $L_{MAX}$ (TS$L_{MAX}$=258) was calculated. Thereafter, the experimental animals (N=10) were re-assigned to groups having $L_{MAX}$ values below (<$L_{MAX}$) or above (>$L_{MAX}$) this TS (FIG. 3A). According to TS$L_{MAX}$ three HF− cows (numbers 1, 5 and 10) were grouped as <$L_{MAX}$ whereas all HF+ and two HF− (number 2 and 6) cows were grouped as >$L_{MAX}$. As shown in FIG. 3B, <$L_{MAX}$ and >$L_{MAX}$ groups differ significantly in their P1 values for HF (19.6±4.0 n.u. vs. 4.7±2.6 n.u, P<0.002), LF (80.4±4.0 n.u. vs. 95.3±2.6 n.u., P<0.002) and $L_{MAX}$ (109.3±26.1 vs. 348.2±17.1, P<0.001).

Characterization of Phenotypic Differences Between Cows Assigned to <$L_{MAX}$ and >$L_{MAX}$ Groups Results from trials in respiratory chambers. To uncover possible phenotypic differences between <$L_{MAX}$ and >$L_{MAX}$ groups all parameters listed in table 4 were re-analysed for the day of ad libitum feeding (P1) and for day 2 of the experiment (P2+P3). In addition, data from a second trial performed during week 2 of lactation (post partum; pp) under the same conditions were used giving us the possibility to explore milk parameters (fat, protein, fat/protein ratio, lactose and energy corrected milk; ECM).

The results are summarized in table 5. In ap cows, BT was significantly higher in <$L_{MAX}$ compared with >$L_{MAX}$ cows during feed deprivation (P2+P3). In addition, pregnant <$L_{MAX}$ cows had higher cortisol levels than those of the >$L_{MAX}$ group during the control ad libitum feeding at day 1 (Table 5). Throughout the complete ap experiment (P1 to P3) cortisol levels differ significantly between <$L_{MAX}$ and >$L_{MAX}$ groups (6.7±0.5 nM/l vs. 5.1±0.3 nM/l, P<0.03).

During the pp experiment $L_{MAX}$ group differences were found at day 2 (P2+P3) for the parameters cortisol peak (maximum value measured at the end of P2), total ghrelin and ECM. Cortisol peak and ghrelin (total) responses, and ECM were all higher in >$L_{MAX}$ compared with <$L_{MAX}$ cows (Table 5).

Results from Experimental Trials Under Normal Housing Conditions.

To further test the possibility that $L_{MAX}$ could predict different phenotypes, data obtained during weeks −5 to −2 (ap) and weeks 2 to 5 (pp) of the joint research project were used (Börner et al., 2013, Schäff et al., 2012). Results of these data re-analysis (N=16 cows) are given in table 6 that summarize parameters differing significantly between >$L_{MAX}$ and <$L_{MAX}$ cows. Of the parameters analysed, only serum insulin concentrations differ during the complete ap period and were much higher (227%) in >$L_{MAX}$ cows. In addition, for >$L_{MAX}$ cows higher DMI (16%) and ECM (13%) were found during the postnatal period. NEFA concentrations however, were different at week +2 only (<$L_{MAX}$: 548±145 μM/l, >$L_{MAX}$; 931±84 μM/l; P=0.0242).

DISCUSSION

General Adaptive Response of Cows to Feed Deprivation

Compared to the period of ad libitum feeding (P1), in all cows HP was significantly reduced during the 10 h feed deprivation (P2) to save energy (Brosh 2007; Derno et al., 2005; Freetly et al., 2006). A reduced blood supply to the portal-drained viscera, mainly the rumen and liver, and thus, a decreased metabolic rate of these organs presumably contribute markedly to energy conservation (Chilliard et al., 1998). All cows also lowered physical activity (reduction of movements, shorter standing times) during P2 which is contrary to experimental results showing that steers (Derno et al., 2005) and calves (Schrama et al., 1995) spend more time standing during energy restriction. Our data suggest a reduction of activity-related HP to be a main component of at least short-term behavioural adaptation to feed deprivation in dairy cows. In accordance with findings showing that the HR of dairy cows must be considered in relation to its metabolic und behavioural status (Brosh, 2007), it was positively correlated with HP during all experimental periods. Our data reveal that under conditions of ad libitum feed intake (P1), the mean HR (72±2 beats/min) was similar to levels reported previously for pregnant, non-lactating cows (Davidson and Beede, 2009; Hagen et al., 2005, Mohr et al., 2002). In all cows, a strong and immediate HR decrease occurs in response to feed removal in P2 and is known to result from a reduced sympathetic activity to the heart (Young and Landsberg, 1977). In addition, reductions in intrinsic heart rate and/or an increased vagal tone can contribute to this effect (Clabough and Swanson, 1989; Després et al., 2002).

In concert with these energy-saving mechanisms, NEFA plasma concentrations are increased indicating that nutrients are provided by lipolysis (Gross et al., 2011; Weber et al., 2013). In addition, a marked elevation (179%) of the growth hormone-releasing and orexigenic peptide hormone ghrelin (Bradford and Allen, 2008; Wertz-Lutz et al., 2006) has been observed in all cows.

During NEB, a reduction of body temperature (BT) and elevated plasma levels of cortisol are physiological mechanisms to reduce energy expenditure and to ensure glucose supply to tissues (Turbill et al., 2011; Samuelsson et al., 1996). However, BT and blood cortisol levels were unchanged by fasting suggesting that under our experimental conditions the metabolic load was not strong enough to induce a response in all cows.

Frequency Domain HRV Analysis Reveals Regulatory Differences Between Cows

Frequency-domain analysis of HRV has been shown to be a sophisticated tool for the detection of ANS regulation of the heart (Yang et al., 2000). However, the distribution of the power and the central frequency of the HRV spectral components also depend on the state of the central nervous system (Cabiddu et al., 2012) and reflect the ANS regulatory capacity and activity in response to psychophysiological stress (Borell von et al., 2007). With regard to its oscillating frequency and underlying mechanism it is categorized into high-frequency (HF) and low-frequency (LF) components (Yang et al., 2000). The LF component jointly represents both parasympathetic and sympathetic tonus (Borell von et al., 2007) whereas the HF component reflects the parasympathetic control (Després et al., 2002; Kézér et al., 2014). The ratio of LF and HF components (LF/HF) mirrors sympatho-vagal balance and is also considered to reflect sympathetic modulation (Stuart et al., 2008; Yang et al., 2000). In our study, by analysing the behaviour of frequency domain HRV parameters it was possible to separate cows showing different autonomic regulation in response to fasting. Cows retrospectively assigned to the HF+ group responded to fasting with increased activity of the parasympathetic branch of the ANS characterized by an HF increase and reduction of the LF/HF ratio (Clabough and Swanson, 1989; Després et al., 2002). In contrast, cows of the HF− group showed a reduction of the HF power accompanied by a 200% increase of the LF/HF ratio. Thus, they reacted to the food removal with a reduction of vagal tone and a shift of their sympatho-vagal balance towards a much stronger dominance of the sympathetic branch of the ANS. In various studies (Gygax et al., 2008; Hagen et al., 2005; Kézér et al., 2014; Mohr et al., 2002; Stuart et al., 2008), a decreased parasympathetic activity has been shown to be associated with stress, reduced well-being, and regulatory capacity. Our data indicate that cows retrospectively assigned to the HF− group experience a higher stress level when food was removed and had a restricted regulatory capacity compared with HF+ cows. Having defined these two groups retrospectively, it was further investigated whether the observed differences could have been predicted by specific HRV indices during control conditions (P1).

It was found that under ad libitum feeding (P1) HF+ and HF− cows differed significantly in the interdependent variables HR and IBI duration and, much more interesting, in $L_{MAX}$. HR and/or mean R-R interval duration are average values based on a 5-minute period integrating the influence of various factors such as ambient temperature, metabolic, and motoric activity. Short-term fluctuations, trends or changes in regulation during this time span are masked which limits their usefulness as predictive markers. In accord regression analysis with $\Delta HF_{P1-P2}$ revealed low $R^2$ values for HR (0.37) and R-R interval (0.33). In contrast to HR and R-R interval, $L_{MAX}$ describes the dynamics of the regulation processes during this 5-minute period. The states of natural systems typically change in time. Those changes can be described by the recurrence plot analysis (RP), where vectors (trajectories) describe the behaviour of elements (points) in a phase space. $L_{MAX}$ describes the longest diagonal line found in the RP. The length of this diagonal line is determined by the duration of similar local evolution of the trajectory segments. The faster the trajectory segments diverge, the shorter are the diagonal lines (Marwan et al, 2007), meaning the system changes between different states. Therefore $L_{MAX}$ is more suitable to describe differences in central autonomic regulation. Indeed, regression analysis with $\Delta HF_{P1-P2}$ results in a high value (0.76) of $R^2$ and allows for calculation of $TSL_{MAX}$ (=258), which is prerequisite to use $L_{MAX}$ for predictive purposes. Of the ten cows used in the present study, 7 cows had $L_{MAX}$ values above 258 (348±17, $>L_{MAX}$ group) and 3 cows had $L_{MAX}$ values below the threshold (109±26, $<L_{MAX}$ group). A shorter $L_{MAX}$ means a higher fluctuation in control of a system, whereas a longer $L_{MAX}$ corresponds to a more deterministic-chaotic character of the time series (Mohr et al., 2002). In our case, $<L_{MAX}$ cows are characterized by a less stable regulation during P1 and the demand of very strong regulation during the metabolic stress of fasting in P2 indicating a restricted regulatory capacity of these animals compared with $>L_{MAX}$ cows. Therefore, it seems conceivable that $L_{MAX}$ can be used to detect alterations in autonomic regulation that might precede metabolic disturbances or a compromised immune function in pregnant and lactating cows in energy deficit.

$L_{max}$ as a Possible Predictor of Disturbed Autonomic Regulation in Response to Metabolic Stress In cows grouped by $L_{MAX}$ several phenotypic differences were observed, most of them during the lactation period and in conjunction with the additional stress of fasting (Table 5 and Table 6).

In pregnant cows the stress parameters BT and cortisol (Kataoka et al, 2014; Willett and Erb, 1972) differ between groups, and both were higher in $<L_{MAX}$ compared with $>L_{MAX}$ cows. For the BT a significant difference between groups were found at day 2 (P2+P3) of the ap experiment, pointing to development of a stress-induced hyperthermia (SIH) in fasting $<L_{MAX}$ cows. SIH means a rise in BT that occurs prior to and during exposure to stress and is different from fever (Vinkers et al., 2010). An ACTH-independent increase in eye temperature has been observed in calves disbudded without local anaesthetic (Stuart et al., 2008). SIH is known to be mediated by the dorsomedial hypothalamus and sympathetic premotor neurons in the rostral medullar raphe region that induce thermogenesis and peripheral vasoconstriction (Kataoka et al., 2014) which is in accord with activation of the sympathetic branch of the ANS in pregnant, fasting $<L_{MAX}$ cows. The plasma level of cortisol is influenced by feeding and by the nutritional status (Chilliard et al. 1998, Samuelsson et al., 1996), and has been shown to increase as an anticipatory response to forthcoming food (Willett and Erb, 1972) and in feed-deprived cows (Mills et al., 1979; Samuelsson et al., 1996). Elevated levels of cortisol are important for glucose supply in animals being in NEB (Samuelsson et al., 1996), but a noticeable increase was only seen in lactating $>L_{MAX}$ cows at day 2 (P2+P3) of the experiment. In addition, peak cortisol levels measured at the end of P2, and reflecting the cortisol response to fasting, were also shown to be significantly higher in $>L_{MAX}$ cows (210% vs. 35% in $<L_{MAX}$ cows).

At the same time point $<L_{MAX}$ and $>L_{MAX}$ cows differ in serum concentrations of total ghrelin. Interestingly, in rodents and humans, ghrelin is possibly involved in the neuroendocrine and behavioral responses to stress (Asakawa et al., 2001; Lambert et al., 2011). The peptide hormone acts at centers of the central nervous system to reduce sympathetic activity (Krapalis et al., 2012; Matsumura et al., 2002), and has been suggested to prevent central stress-induced sympathoactivation (Asakawa et al., 2001; Lambert et al., 2011). Moreover, adrenocorticotrophic hormone (ACTH), cortisol, and epinephrine, but not norepinephrine a global marker of overall sympathetic nervous system activity, increase after ghrelin application (Krapalis et al., 2012; Matsumura et al., 2002). Higher total ghrelin levels as observed in $>L_{MAX}$ cows might thus have a sympatholytic effect.

The results confirm a higher stress level and instable regulatory processes in $<L_{MAX}$ cows which is also in accord with the marked reduction (about 10 kg/day) of energy corrected milk yield that has been observed.

In this context it is interesting to note that $L_{MAX}$ grouping of cows (N=16) and re-analysis of data obtained under normal housing conditions (Börner et al., 2013, Schäff et al., 2012) also reveal differences between $<L_{MAX}$ and $>L_{MAX}$ groups. Compared to cows of the $>L_{MAX}$ group, cows of the $<L_{MAX}$ group had lower blood insulin levels during weeks −5 to −2 ap and showed constantly lower DMI and ECM during weeks 2 to 5 of lactation. Altogether, these results point to $L_{MAX}$ being a predictive tool for identifying animals at risk and selecting highly adaptable and robust animals.

CITED LITERATURE

Asakawa A, Inui A, Kaga T, Yuzuriha H, Nagata T, Fujimiya M, Katsuura G, Makino S, Fujino M A and Kasuga M 2001. A role of ghrelin in neuroendocrine and behavioral responses to stress in mice. Neuroendocrinology 74, 143-147.

Borell von E, Langbein J, Despres G, Hansen S, Leterrier C, Marchant-Forde J, Marchant-Forde R, Minero M, Mohr E, Prunier A, Valance D and Veissier I 2007. Heart rate variability as a measure of autonomic regulation of cardiac activity for assessing stress and welfare in farm animals—a review. Physiology &. Behavior 92, 293-316.

Börner S, Albrecht E, Schäff C, Hacke S, Kautzsch U, Derno M, Hammon H M, Röntgen M, Sauerwein H and Kuhla B 2013. Reduced AgRP activation in the hypothalamus of cows with high extent of fat mobilization after parturition. General and Comparative Endocrinology, 193, 167-177.

Bradford B J, and Allen M S 2008. Negative energy balance increases periprandial ghrelin and growth hormone concentrations in lactating dairy cows. Domestic Animal Endocrinology 34, 196-203.

Brosh, A 2007. Heart rate measurements as an index of energy expenditure and energy balance in ruminants: a review. Journal of Animal Science 85, 1213-1227.

Brouwer, E 1965. Report of sub-committee on constants and factors. Energy Metabolism. Proc 3rd Symposium 11: 441-443. Troon UK, EAAP. Blaxter, K. L.

Cabiddu R, Cerutti S, Viardot G, Werner S and Bianchi A M 2012. Modulation of the sympatho-vagal balance during sleep: frequency domain study of heart rate variability and respiration. Frontiers in Physiology 3, 45. doi: 10.3389/fphys.2012.00045.

Chilliard Y, Bocquier F and Doreau M 1998. Digestive and metabolic adaptations of ruminants to undernutrition, and consequences on reproduction. Reproduction Nutrition Development 38, 131-152.

Clabough D L and Swanson C R 1989. Heart rate spectral analysis of fasting-induced bradycardia of cattle. American Journal of Physiology 257, R1303-R1306.

Davidson J A and Beede D K 2009. Exercise training of late-pregnant and nonpregnant dairy cows affects physical fitness and acid-base homeostasis. Journal of Dairy Science 92, 548-562.

Derno M, Jentsch W, Schweigel M, Kuhla S, Metges C C and Matthes H D 2005. Measurements of heat production for estimation of maintenance energy requirements of Hereford steers. Journal of Animal Science 83, 2590-2597.

Després G, Veissier I and Boissy A 2002. Effect of autonomic blockers on heart period variability in calves: Evaluation of the sympatho-vagal balance. Physiological Research 51, 347-353.

Freetly H C, Nienaber J A and Brown-Brandl T 2006. Changes in heat production by mature cows after changes in feeding level. Journal of Animal Science 84, 1429-1438.

Fröhli D and Blum J W 1988. Effects of fasting on blood plasma levels, metabolism and metabolic effects of epinephrine and norepinephrine in steers. Acta Endocrinologica 118, 254-259.

Gross J J, van Dorland H A, Bruckmaier R M and Schwarz F J. 2011. Performance and metabolic profile of dairy cows during a lactational and deliberately induced negative energy balance with subsequent realimentation. Journal of Dairy Science 94, 1820-1830.

Gygax L, Neuffer I, Kaufmann C, Hauser R and Wechsler B 2008. Restlessness behaviour, heart rate and heart-rate variability of dairy cows milked in two types of automatic milking systems and auto-tandem milking parlours. Applied Animal Behaviour Science 109, 167-179.

Hagen K, Langbein J, Schmied C, Lexer D and Waiblinger S 2005. Heart rate variability in dairy cows-influences of breed and milking system. Physiology & Behavior 85, 195-204.

Kataoka N, Hioki H, Kaneko T and Nakamura K 2014. Psychological stress activates a dorsomedial hypothalamus-medullary raphe circuit driving brown adipose tissue thermogenesis and hyperthermia. Cell Metabolism 20, 346-358.

Kennedy J, Dillon P, Delaby L, Faverdin P, Stakelum G and Rath M 2003. Effect of genetic merit and concentrate supplementation on grass intake and milk production with Holstein Friesian dairy cows. Journal of Dairy Science 86, 610-621.

Kézér F L, Kovacs L, Jurkovich V, Szenci O and Tözsér J 2014. Heart rate variability as non-invasive measure of stress in cattle—field studies on Hungarian dairy herds. Hungarian Agricultural Research 4, 33-38.

Krapalis A F, Reiter J, Machleidt F, Iwen K A, Dodt C, Lehnert H and Sayk F 2012. Ghrelin modulates baroreflex-regulation of sympathetic vasomotor tone in healthy humans. American Journal Physiology Regulatory Integrative Comparative Physiology 302, R1305-R1312.

Lambert E, Lambert G, Ika-Sari C, Dawood T, Lee K, Chopra R, Straznicky N, Eikelis N, Drew S, Tilbrook A, Dixon J, Esler M and Schlaich M P 2011. Ghrelin modulates sympathetic nervous system activity and stress response in lean and overweight men. Hypertension 58, 43-50.

Marwan N, Carmen Romano M, Thiel M and Kurths J 2007. Recurrence plots for the analysis of complex systems. Physics Reports 438, 237-329.

Matsumura K, Tsuchihashi T, Fujii K, Abe I and Iida M 2002. Central ghrelin modulates sympathetic activity in conscious rabbits. Hypertension 40, 694-699.

Mills S E, and Jenny B F 1979. Effects of high concentrate feeding and fasting on plasma glucocorticoids in dairy heifers. Journal of Animal Science 48, 961-969.

Mohr E, Langbein J and Nürnberg G 2002. Heart rate variability: a noninvasive approach to measure stress in calves and cows. Physiology & Behavior 75, 251-259.

Mudron P, Rehage J, Sallmann H P, Holtershinken M and Scholz H 2005. Stress response in dairy cows related to blood glucose. Acta Veterinaria Brno 74, 37-42.

Samuelsson B, Uvnäs-Moberg K, Gorewit R C and Svennersten-Sjaunja K 1996. Profiles of the hormones somatostatin, gastrin, CCK, prolactin, growth hormone and cortisol. II. In dairy cows that are milked during food deprivation. Livestock Production Science 46, 57-64.

Schäff C, Börner S, Hacke S, Kautzsch U, Albrecht D, Hammon H M, Röntgen M and Kuhla B. 2012. Increased anaplerosis, TCA cycling and oxidative phosphorylation in the liver of dairy cows with intensive body fat mobilization during early lactation. Journal of Proteome Research 11, 5503-5514.

Schrama J W, Roefs J P, Gorssen J, Heetkamp M J and Verstegen M W. 1995. Alteration of heat production in young calves in relation to posture. Journal of Animal Science. 73, 2254-2262.

Stuart M, Stafford K J, Dowling S K, Schaefer A L and Webster J R 2008. Eye temperature and heart rate variability of calves disbudded with or without local anaesthetic. Physiology & Behavior 93: 789-797.

Task Force of the European Society of Cardiology and The North American Society for Pacing and Electrophysiology 1996. Heart Rate Variability: Standards of measurement, physiological interpretation, and clinical use. European Heart Journal 17, 354-381.

ThidarMyint H, Yoshida H, Ito T and Kuwayama H 2006. Dose-dependent response of plasma ghrelin and growth hormone concentrations to bovine ghrelin in Holstein heifers. Journal of Endocrinology 189, 655-664.

Thun R, Eggenberger E, Zerobin K, Luscher T and Vetter W 1981. Twenty-four-hour secretory pattern of cortisol in the bull: evidence of episodic secretion and circadian rhythm. Endocrinology 109, 2208-2212.

Turbill C, Ruf T, Mang T and Arnold W 2011. Regulation of heart rate and rumen temperature in red deer: effects of season and food intake. The Journal of Experimental Biology 214, 963-970.

Vinkers C H, Penning R, Ebbens M M, Hellhammer J, Verster J C, Kalkman C J and Olivier B 2010. Stress-induced hyperthermia in translational stress research. The Open Pharmacology Journal 4, 30-35.

Weber C, Hametner C, Tuchscherer A, Losand B, Kanitz E, Otten W, Singh S P, Bruckmaier R M, Becker F, Kanitz W and Hammon H M 2013. Variation in fat mobilization during early lactation differently affects feed intake, body condition, and lipid and glucose metabolism in high-yielding dairy cows. Journal Dairy Science 96, 1-16.

Wertz-Lutz A E, Knight T J, Pritchard R H, Daniel J A, Clapper J A, Smart A J, Trenkle A and Beitz, D C 2006. Circulating ghrelin concentrations fluctuate relative to nutritional status and influence feeding behavior in cattle. Journal of Animal Science 84, 3285-3300.

Willett L B, and Erb R E 1972. Short term changes in plasma corticoids in dairy cattle. Journal of Animal Science 34, 103-111.

Yang C C H, Chao T C, Kuo T B J, Yin C S and Chen H I 2000. Preeclamptic pregnancy is associated with increased sympathetic and decreased parasympathetic control of HR. American Journal of Physiology Heart and Circulation Physiology 278, H1269-H1273.

Young J B and Landsberg L 1977. Suppression of sympathetic nervous system during fasting. Science 196, 1473-1475.

DE 20 2012 100 735.5

What claimed:

1. A computer-implemented method for identifying a farm animal having an impairment of regulative capacity in response to metabolic stress, the method comprising:
   a) assessing a value of a nonlinear domain heart rate variability component $L_{MAX}$ of a farm animal of a species based on a heart beat interval data set obtained for the farm animal;
   b) comparing the value of $L_{MAX}$ assessed according to (a) with a species specific threshold of $L_{MAX}$; and
   c) identifying the farm animal as having an impairment of regulative capacity when its value of $L_{MAX}$ is below the species specific threshold, wherein the method further comprises determining the species specific threshold of $L_{MAX}$ by performing the following steps:
      i) determining the value of the nonlinear domain heart rate variability component $L_{MAX}$ of at least two farm animals of the species to be assessed based on heart beat interval data sets obtained for the at least two farm animals from a feed-ad-libitum-period ($L_{MAX\ ad\ libitum}$);
      ii) determining a value of a high frequency domain parameter of heart rate variability (HF) of the at least two farm animals as in (i) based on the heart beat interval data sets obtained for the at least two farm animals from a feed-ad-libitum-period ($HF_{ad\ libitum}$);
      iii) determining the value of the high frequency domain parameter of heart rate variability (HF) of the at least two farm animals as in (i) based on the heart beat interval data sets obtained for the at least two farm animals from a fasting-period ($HF_{fasting}$);
      iv) determining a difference between $HF_{ad\ libitum}$ and $HF_{fasting}$ ($\Delta HF$) for each of the at least two farm animals;
      v) performing a linear regression of $\Delta HF$ versus $L_{MAX\ ad\ libitum}$; and
      vi) determining the species specific threshold of $L_{MAX}$ in that the value of $L_{MAX\ ad\ libitum}$ corresponding to $\Delta HF$=zero in the linear regression according to (v) represents the species specific threshold of $L_{MAX}$.

2. The method according to claim 1, wherein the farm animal is selected from the group of species consisting of horse, cow, pig and goat.

3. The method according to claim 1, wherein the heart beat interval data set obtained for the farm animal according to a) are heart beat interval data of a feed-ad-libitum-period.

4. The method of claim 1, wherein the species specific threshold of $L_{MAX}$ for dairy cows is in the range of from 200 to 300.

5. The method according to claim 2, wherein the farm animal is a cow.

6. The method according to claim 5, wherein the farm animal is a dairy cow.

7. The method of claim 4, wherein the species specific threshold of $L_{MAX}$ for dairy cows is in the range of from 220 to 280.

8. The method of claim 7, wherein the species specific threshold of $L_{MAX}$ for dairy cows is in the range of from 250 to 270.

9. The method of claim 8, wherein the species specific threshold of $L_{MAX}$ for dairy cows is in the range of from 255 to 265.

10. The method of claim 9, wherein the species specific threshold of $L_{MAX}$ for dairy cows is 258.

* * * * *